(12) United States Patent
Friedrich et al.

(10) Patent No.: US 12,138,579 B2
(45) Date of Patent: Nov. 12, 2024

(54) TWO-STAGE METHOD FOR RECOVERING HALOGENATED HYDROCARBONS

(71) Applicant: ZEOSYS MEDICAL GMBH, Luckenwalde (DE)

(72) Inventors: Thomas Friedrich, Berlin (DE); Christian Ewers, Luckenwalde (DE)

(73) Assignee: ZEOSYS MEDICAL GMBH, Luckenwalde (DE)

( * ) Notice: Subject to any disclaimer, the term of this patent is extended or adjusted under 35 U.S.C. 154(b) by 473 days.

(21) Appl. No.: 17/428,636

(22) PCT Filed: Feb. 4, 2020

(86) PCT No.: PCT/EP2020/052713
§ 371 (c)(1),
(2) Date: Aug. 5, 2021

(87) PCT Pub. No.: WO2020/161115
PCT Pub. Date: Aug. 13, 2020

(65) Prior Publication Data
US 2022/0111326 A1     Apr. 14, 2022

(30) Foreign Application Priority Data
Feb. 5, 2019   (EP) .................................... 19155562

(51) Int. Cl.
*B01D 53/04* (2006.01)
*C07C 17/389* (2006.01)
*C07C 41/36* (2006.01)

(52) U.S. Cl.
CPC ..... *B01D 53/0438* (2013.01); *B01D 53/0415* (2013.01); *C07C 17/389* (2013.01);
(Continued)

(58) Field of Classification Search
CPC .............................. C07C 17/389; C07C 41/36
See application file for complete search history.

(56) References Cited

U.S. PATENT DOCUMENTS

| 3,332,854 | A | 7/1967 | Duckstein |
| 4,462,904 | A | 7/1984 | Hager |
| (Continued) | | | |

FOREIGN PATENT DOCUMENTS

| DE | 102006027127 | 12/2007 |
| DE | 102007048892 | 4/2009 |
| (Continued) | | |

OTHER PUBLICATIONS

Machine translation of international publication WO2004071268A2, Aug. 26, 2004 (Year: 2004).*

*Primary Examiner* — Medhanit W Bahta
(74) *Attorney, Agent, or Firm* — JMB DAVIS BEN-DAVID

(57) ABSTRACT

The invention relates to a two-stage method for recovering halogenated hydrocarbons. In a desorption step, steam is passed through an adsorbent comprising adsorbed halogenated hydrocarbons, which produces a secondary flow volume containing halogenated hydrocarbons. The secondary flow volume is converted into a condensate containing halogenated hydrocarbons and water by cooling, from which condensate the halogenated hydrocarbons are separated. In a sterilisation step that precedes the desorption step, the adsorbent comprising adsorbed halogenated hydrocarbons is brought into contact with steam for at least 10 minutes at a temperature of more than 120° C. and at a pressure between 0.15 MPa and 0.4 MPa.

12 Claims, 3 Drawing Sheets

(52) U.S. Cl.
CPC ........ *C07C 41/36* (2013.01); *B01D 2253/102* (2013.01); *B01D 2253/108* (2013.01); *B01D 2257/2066* (2013.01); *B01D 2259/4009* (2013.01); *B01D 2259/4533* (2013.01)

(56) References Cited

U.S. PATENT DOCUMENTS

| | | |
|---|---|---|
| 2009/0101010 A1 | 4/2009 | Fuesting |
| 2015/0283494 A1* | 10/2015 | Welke .................. B01J 20/3408 62/636 |
| 2016/0023157 A1 | 1/2016 | Matthias et al. |
| 2016/0096793 A1 | 4/2016 | Filipovic et al. |
| 2017/0056610 A1 | 3/2017 | Hunt et al. |

FOREIGN PATENT DOCUMENTS

| | | |
|---|---|---|
| EP | 0284227 | 9/1988 |
| EP | 2926897 | 10/2015 |
| JP | H06226045 | 8/1994 |
| WO | 2004071268 | 8/2004 |

* cited by examiner

TWO-STAGE METHOD FOR RECOVERING HALOGENATED HYDROCARBONS

CROSS-REFERENCE TO RELATED APPLICATIONS

This is the U.S. National Stage of International Patent Application No. PCT/EP2020/052713 filed on Feb. 4, 2020, which in turn claims the benefit of European Patent Application No. 19155562.2 filed on Feb. 5, 2019.

BACKGROUND

Inhalation anesthetics are administered to induce or maintain anesthesia in a patient. The inhalation anesthetics administered are predominantly released back into the environment via the patient's breathing air, which is why they are continuously extracted in operating rooms and disposed of via the roof, to the detriment of the environment. This is because inhalation anesthetics from the flurane class consist of halogenated hydrocarbons. These are potent greenhouse gases and ozone layer depleting. The recovery of inhalation anesthetics from the air breathed by patients is therefore essential to protect the health of hospital staff in unventilated regions), for environmental reasons, and also from an economic point of view.

Apparatuses and processes are already known with which inhalation anesthetics can be both adsorbed and desorbed from patients' breathing air on filter materials.

EP15166625 describes a filter system for a building, in particular for a hospital, which is set up to filter out anesthetic gases from the gas mixture flowing through the filter system.

EP15162339 discloses a device for recovering anesthetic gases, in particular halogenated hydrocarbons, which is adapted to desorb halogenated hydrocarbons adsorbed on filter materials by means of steam.

EP08701206 and EP07787403 describe a process and a filter for adsorption of halogenated hydrocarbons and their subsequent desorption from the filter.

WO2007093640 describes a filter cartridge arranged for adsorption and desorption of halogenated hydrocarbons.

In order to reuse recovered inhalation anesthetics for anesthetizing patients, it is necessary to sterilize the inhalation anesthetics. No processes and no devices are yet known from the prior art that are designed to recover and sterilize inhalation anesthetics in one process.

Objective of the Invention

Therefore, the objective of the invention is to provide a process and an apparatus for improved recovery of inhalation anesthetics. This objective is solved by a process for recovering halogenated hydrocarbons according to the claims.

Definitions

The term adsorbent or sorbent, in the context of the present description, refers to a material that can adsorb gases on its surface. Adsorbent and sorbent are used interchangeably in the present invention.

The term sorbate refers to the adsorbent with the gases adsorbed thereon.

The term desorbate denotes the desorbed gases.

The term sorptive refers to the gases to be adsorbed.

The term halogenated hydrocarbons is to be understood in the present description as referring to fluorine-containing inhalation anesthetics.

DETAILED DESCRIPTION OF THE INVENTION

A first aspect of the invention relates to a process for the recovery of halogenated hydrocarbons. In this process, in a desorption step, an adsorbent comprising adsorbed halogenated hydrocarbons is streamed through by a volume flow essentially consisting of dry water vapor at an elevated temperature, (wherein in particular the adsorbent comprising adsorbed halogenated hydrocarbons is flown through by water vapor). As a result, the adsorbed halogenated hydrocarbons are desorbed by the adsorbent and absorbed into the volume flow, resulting in a secondary volume flow comprising halogenated hydrocarbons and water vapor. This secondary volume flow is converted by cooling into a condensate containing halogenated hydrocarbons and water. The halogenated hydrocarbons are separated from this condensate. The temperature is in particular at or above 100° C. during this step. Various process variants envision this step being carried out in particular at a temperature of 100 to 150° C., in particular at a temperature of 120° C. to 150° C.

According to the invention, the desorption step is preceded by a sterilization step. Thereby, in particular the sorbate is exposed to water vapor of a hot water vapor atmosphere before flowing through. The inventors have determined the parameters of this step which are necessary and sufficient to treat active ingredients recovered from sorbates potentially contaminated with pathogenic organisms in such a way that they comply with the regulations of the European drug authorities regulations and analogous regulations of other countries. In particular, the desorption step and the sterilization step are carried out in direct sequence in order to increase the effectiveness of the process. However, it is also conceivable to provide a pause between the desorption step and the sterilization step. Furthermore, the desorption step and the sterilization step can in particular be carried out in the same installation or in different installations. For example, a desorption vessel can first be coupled to a sterilization installation and then to a desorption installation.

According to the invention, during the sterilization step, the adsorbent comprising the adsorbed halogenated hydrocarbons is brought into contact with in particular dry water vapor for at least 10 min, in particular for 10 min to 60 min, at a temperature of more than 120° C., in particular at a temperature of 121° C. to 150° C., and at a pressure of 0.15 MPa to 0.4 MPa, in particular at a pressure of 0.15 MPa to 0.3 MPa.

In an embodiment, the adsorbent comprising the adsorbed halogenated hydrocarbons is brought into contact with, in particular dry, water vapor for 20 min to 40 min, in particular for about 30 min, at a temperature of 135° C. to 145° C., and a pressure of 0.24 MPa to 0.26 MPa.

By combining the parameters of sterilization-time, -temperature and -pressure, conditions are created in which complete inactivation of all pathogens present in the sorbate is ensured. At the same time, the above parameters of sterilization-time, -temperature and -pressure are selected in such a way that the adsorbed halogenated hydrocarbons do not decompose or undergo chemical reactions under the prevailing conditions, so that the sterilized halogenated hydrocarbons can be used again after desorption.

According to an embodiment, water vapor does not flow through the adsorbent during the sterilization step. According to an embodiment, the water vapor flows through the adsorbent particularly once, during the introduction of the water vapor, and then remains in a vapor atmosphere at positive pressure. In particular, only after the sterilization step is completed, the adsorbent is streamed through by the water vapor for desorption of the halogenated hydrocarbons.

The build-up of pressure in the sterilization step and the flow of water vapor through the adsorbent in the desorption step can be controlled, for example, by opening and closing a valve of a desorption vessel. Alternatively, other manual means may be provided to perform the steps of the process. For example, a desorption vessel could be manually connected in sequence to conduits of a sterilization installation and a desorption installation, wherein pressure is built up in the vessel by means of the sterilization installation and subsequently a volume flow is generated in the vessel by means of the desorption installation.

According to a further embodiment, the sterilization step and the desorption step are carried out in direct sequence in a desorption vessel in the same installation.

For desorption, the water vapor is passed through the sorbate in particular so that a steady flow of water vapor through the sorbate enables the halogenated hydrocarbons to be absorbed into the water vapor and thus removed. A mixture of water vapor and halogenated hydrocarbons is formed.

This mixture is, according to an embodiment of the process, freed from the entrained impurities and brought to a temperature below 30° C. A two-phase liquid mixture, the condensate, is formed. The halogenated hydrocarbons are separated from this condensate and further processed. The water can be returned to the process.

According to a further embodiment, the mixture of water vapor and halogenated hydrocarbons is brought to a temperature below 70° C., in particular below 65° C., further in particular below 60° C., further in particular below 55° C., further in particular below 50° C., further in particular below 45° C., to form a two-phase liquid mixture (or condensate), further in particular below 40° C., further in particular below 35° C., further in particular below 30° C., further in particular below 25° C., further in particular below 20° C., further in particular below 15° C., further in particular below 10° C., further in particular below 5° C., wherein the mixture is previously freed in particular from the entrained impurities. In particular, a two-phase liquid mixture, the condensate, is thereby formed, wherein the halogenated hydrocarbons are separated and further processed. In particular, the water can be recycled into the process.

The temperature to which the mixture is brought to produce the condensate can be selected depending on the boiling temperature of the halogenated hydrocarbon to be desorbed. In this case, the temperature must be below the boiling temperature of the respective hydrocarbon.

In addition, the temperature can be optimized to minimize the gas fraction above the desorbate-water mixture, which typically forms when the heavier phase sinks, to minimize losses via the gas phase. In addition to the boiling temperature of the respective halogenated hydrocarbon, process control parameters are also taken into account when selecting the temperature to which the condensate is brought. For example, temperatures that are too low can cause coolers or conduits to freeze, which negatively affects the process. For example, the boiling temperatures of some common inhalation anesthetics are as follows: sevoflurane: 58.5° C., isoflurane: 48.5° C., desflurane: 22.5° C., enflurane: 56.5° C., halothane: 50.2° C. After desorption of the halogenated hydrocarbons, the sorbent is in particular cooled. The now sorptive-free sorbent can be provided for further adsorption/desorption cycles.

According to a further embodiment, the adsorbent at which the halogenated hydrocarbons are adsorbed is activated carbon, in particular hydrophobic activated carbon, and/or zeolite, in particular hydrophobic zeolite, in particular modified hydrophobic zeolite. The adsorbent is in particular porous and comprises pores, in particular in the region of micrometers and/or nanometers. An adsorbent mixture can also be used.

According to a further embodiment of the invention, the adsorbent is characterized, prior to adsorption or after the entire process cycle has been carried out and prior to use for adsorption of anesthetics, by a water content of ≤5% (w/w), in particular by a water content of ≤2% (w/w). This water content may change during the course of the process.

Adsorbents can be both hydrophilic and hydrophobic. In particular hydrophobic adsorbents are used for the present process. Hydrophobic adsorbents can also absorb large quantities of water. Adsorption is only possible at the sites of the adsorbent not occupied by water. Thus, the adsorbent used according to the invention should in particular comprise the lowest possible water content in order to be able to absorb as much halogenated hydrocarbons as possible. After desorption of the halogenated hydrocarbons, the adsorbent may comprise e.g. a water content of more than 30% (w/w). After removal of most of the water, the adsorbent can be reused.

According to a further embodiment, the water vapor used in the desorption step essentially contains no liquid water, in particular less than 0.1 weight percent of liquid water, further in particular no liquid water.

A distinction is made between wet steam and superheated steam. Superheated steam is steam that comprises a temperature above the boiling temperature of water at the given pressure. Superheated steam therefore no longer contains liquid water. With wet steam, there is always a portion of water droplets in the steam.

According to a further embodiment, the steam used is pure steam. Pure steam is obtained by evaporating fully demineralized water.

According to a further embodiment, the halogenated hydrocarbons comprise fluorine-containing inhalation anesthetics or are fluorine-containing inhalation anesthetics, particularly sevoflurane, isoflurane, enflurane, halothane, desflurane, or mixtures thereof.

According to a further embodiment, the adsorbent comprising the halogenated hydrocarbons was obtained by filtering breathing air from the treatment of patients anesthetized with halogenated hydrocarbons.

According to a further embodiment of the process, the sterilization step and the desorption step are performed in a desorption vessel that is pressure stable up to 0.4 MPa. The desorption vessel comprises in particular at least one steam inlet and at least one steam outlet. In particular, steam is fed into the desorption vessel via the steam inlet and leaves the desorption vessel in particular via the steam outlet. The adsorbent comprising the adsorbed halogenated hydrocarbons is arranged between the steam inlet and the steam outlet in the desorption vessel such that steam entering the desorption vessel through the steam inlet must pass through the adsorbent before leaving the desorption vessel through the steam outlet. Each point of the adsorbent comprising the adsorbed halogenated hydrocarbons thus comes into contact with the steam. As steam flows through the adsorbent, in particular a temperature gradient is formed from the steam inlet to the steam outlet. The coldest point in the desorption vessel is thus in particular at the steam outlet. A temperature sensor is installed at this location. According to an embodiment of the invention, the desorption vessel comprises a valve which is downstream of the steam outlet, wherein the valve is closed during the sterilization step and is open during the desorption step. Thus, the required pressure in the desorption vessel can be established during the sterilization step. During the desorption step, the valve is in particular open so that the secondary volume flow can leave the desorption vessel via the steam outlet. The adsorbent comprising the halogenated hydrocarbons may be, according to an embodiment, contained in the desorption vessel in an adsorbent container removable from the desorption vessel.

The desorption vessel comprises according to an embodiment a circumferential wall and a bottom terminating with the circumferential wall, wherein the bottom in particular is a curved bottom, in particular a dished ("Klopper") bottom according to DIN 28011. In particular due to its curvature, the bottom forms a cavity below the adsorbent container introduced into the desorption vessel and is configured to receive a condensate. The condensate comprises in particular condensed gases. The condensate may comprise water vapor as well as the halogenated hydrocarbons. The bottom is not necessarily designed as a dished ("Klopper") bottom, but is advantageous for the process according to the invention, since the desorbate-water mixture can thus be passed through the outlet valve without leaving any residue. The bottom, according to an embodiment, is designed to absorb the maximum possible quantity of condensate under operating conditions. The quantity of condensate absorbed depends on the temperature difference to the desorption vessel. In certain embodiments, it is intended to still preheat the bottom of the vessel to keep the quantity of condensate as low as possible. A residual amount of condensate is difficult to avoid in most operating conditions, since once a condensate amount is formed, it cannot be completely transferred to the gas phase by the subsequent steam due to the small heat transfer surface.

According to a further embodiment, the bottom of the desorption vessel comprises a first shell and a second shell, wherein a space is formed between the first shell and the second shell, and wherein steam is introduced into the space, in particular during the sterilization step, so that the bottom is heated.

The temperature prevailing in the desorption vessel is measured and controlled in particular by a temperature sensor. The temperature sensor is located below the adsorbent container introduced into the desorption vessel, in particular between the steam outlet and the adsorbent container introduced into the desorption vessel, in particular immediately below the adsorbent container introduced into the desorption vessel.

The temperature sensor is located, according to an embodiment, immediately below the adsorbent container. Thereby, the temperature sensor is arranged such that the sensor element is located exactly below the bottom of the adsorbent container. The temperature sensor thus always measures the temperature of the vapor phase and not that of the condensate, which can accumulate in the region of the bottom of the desorption vessel. According to an embodiment, the temperature sensor is configured to control the process. As soon as a predefined sterilization temperature is reached during the sterilization step, a set sterilization time is measured. After the sterilization time has elapsed, the sterilization step is terminated. This can take place by opening the valve and thus initiating the desorption step. According to a further embodiment, a controller is provided for controlling the process, wherein the controller is formed to control the process on the basis of the temperature measured by the temperature sensor, particularly of the vapor phase.

According to an embodiment, the temperature sensor is used to monitor and control the process according to the invention, but only to the extent that the sterilization process is restarted when the temperature falls below the set temperature. There is in particular no connection with the steam generator in the process. In these embodiments, the process itself is in particular only operated pressure-wise above the set operating pressure.

According to an embodiment, the temperature sensor is used to monitor and control the process according to the invention by directly controlling the steam generator and, if applicable, the connected valves.

According to an embodiment, the desorption vessel comprises two adsorbent containers arranged one above the other. The adsorbent containers are in particular supplied with steam through two steam inlets respectively arranged above or upstream of the adsorbent containers. By accommodating two adsorbent containers, each with its own steam inlet, the temperature gradient within the adsorbent is reduced. Sterilization is thus feasible even at a lower steam temperature, compared to an apparatus with only one steam inlet, at any point of the adsorbent. Of course, the desorption vessel may also comprise three or more adsorbent containers arranged one above the other in an analogous manner.

The adsorbent container comprises, according to an embodiment, a circumferential wall, a bottom and/or a lid terminating with the circumferential wall. According to a further embodiment, the bottom and/or the lid comprises a gas-permeable filter fabric, or consists thereof.

The filter fabric comprises, according to an embodiment, pores ranging from 10-100 µm, in particular in a region of 20-50 µm, in particular of 40 µm.

According to a further embodiment, the filter fabric comprises pores of a pore size ranging from 10 nm to 100 µm, in particular 100 nm to 100 µm, further in particular 1 µm to 100 µm, wherein the pores may in particular be of different sizes.

The adsorbent container(s) can be introduced into the desorption vessel.

The wall of the adsorbent container does in particular not contact the wall of the desorption vessel, forming a space between the wall of the desorption vessel and the wall of the adsorbent container.

To prevent steam flow in the space between the adsorbent container and the desorption vessel, the lid of the adsorbent container is provided, according to an embodiment, with a seal so that steam must pass through the adsorbent container. This seal is an inflatable profile seal.

According to a further embodiment, a seal, in particular a circumferential seal, is provided between the desorption vessel and the adsorbent container (or each adsorbent container in the case of several adsorbent containers), which closes the space between the desorption vessel and the adsorbent container, in particular in a gas-tight manner. In particular, the seal is arranged at the level of an upper edge of the adsorbent container (or the respective adsorbent container) when the (respective) adsorbent container is introduced into the desorption vessel. In particular, the seal is deformed by means of an overpressure (e.g., of an inert gas, e.g., of up to 0.12 MPa above the process pressure prevailing in the desorption vessel) so that the seal closes the space, in particular in a gas-tight manner (in particular wherein the seal is pressed against an outer wall of the adsorbent container or against an inner wall of the desorption vessel). According to one embodiment, the seal is deformed only during the desorption step by means of the overpressure. During the sterilization step, the seal is in particular not subjected to overpressure, so that a stable steam atmosphere can form (also in the space between the adsorbent container and the desorption vessel).

Another aspect of the process is the recovery of the halogenated hydrocarbons in the recovery step. For this purpose, the secondary volume flow, which leaves the desorption vessel, according to an embodiment, via the vapor outlet, is freed of the entrained impurities via a collector line by means of an in particular rinsable pre-filter and an in particular rinsable post-filter. According to an embodiment, the secondary volume flow is brought to a temperature of below 30° C. by subsequent coolers, in particular three of such downstream coolers. According to a further embodiment, the secondary volume flow is brought to a temperature of below 70° C., in particular below 65° C., further in particular below 60° C., further in particular below 55° C., further in particular below 50° C., further in particular below 45° C., further in particular below 40° C., further in particular below 35° C., further in particular below 30° C., further in particular below 25° C., further in particular below 20° C., further in particular below 15° C., further in particular below 10° C., further in particular below 5° C., by subsequent coolers, in particular three such subsequent coolers.

After the last cooler, the condensate-water mixture formed in this way is transferred in particular to a condensate collection container. A two-phase liquid mixture is formed. In particular, the halogenated hydrocarbons are separated from this condensate and further processed. The water can be returned to the evaporation process.

A further aspect of the present invention comprises an apparatus for carrying out the illustrated two-step process of recovering halogenated hydrocarbons. This apparatus comprises a pressure stable desorption vessel. This desorption vessel comprises
- a steam inlet configured to admit steam into the desorption vessel, in particular to connect with a steam generator,
- a steam outlet configured to discharge steam from the desorption vessel, with an outlet arranged downstream of the steam outlet in the direction of steam discharge,
- a valve by which the outlet can be closed,
- a space in particular between the steam inlet and the steam outlet, which is designed to receive a bulk material, e.g. an adsorbent comprising halogenated hydrocarbons.

The steam required for the process can be generated in particular by a steam generator which is part of the apparatus according to the invention. Alternatively, a separate, external steam generator can also be connected to the steam inlet of the apparatus.

The formation of the condensate according to the process according to the invention can take place, in particular within the desorption vessel or in a separate condensation section or condensation vessel.

The valve is in particular pressure-stable to close to at least a pressure of 0.4 MPa. The valve is in particular configured to control the pressure within the desorption vessel. When the valve is closed, it is in particular configured to allow pressure to build up within the desorption vessel. The steam outlet is in particular blocked when the valve is closed. When the valve is open, a volume flow can leave the desorption vessel in particular via the steam outlet.

According to an embodiment of the apparatus according to the invention, the desorption vessel comprises at least one removable adsorbent container provided for receiving the bulk material and a temperature sensor, which is arranged on the or on a side of the adsorbent container facing the steam outlet thus on the side facing away from the steam inlet. The temperature sensor is arranged in particular immediately below the adsorbent container. Thereby, the adsorbent container forms in particular at least a part of the space, in particular the entire space, which is configured to receive the bulk material. In the case of multiple adsorbent containers, the multiple adsorbent containers in particular jointly form said space for receiving the bulk material.

According to an embodiment of the apparatus, the temperature sensor is connected to a control device, which is designed to open the valve after a target temperature has been reached and/or after a preselected time period, in particular of 10 min to 60 min, during which the target temperature is maintained, has elapsed. The control device can be outside the desorption vessel.

According to a further embodiment, the desorption vessel comprises a curved bottom, in particular a dished ("Klopper") bottom according to DIN 28011. The bottom is in particular configured to absorb condensed portions during the sterilization step.

According to a further embodiment, the desorption vessel is pressure-stable up to 0.4 MPa. According to a further embodiment, the desorption vessel is configured to receive two adsorbent containers arranged one above the other, and with two steam inlets respectively arranged above the adsorbent containers.

According to a further embodiment, the apparatus comprises a steam generator configured to generate in particular dry steam, wherein the steam generator is in fluid communication or connected to at least one steam inlet.

According to a further embodiment, the apparatus comprises a drying device downstream of the steam generator, wherein the drying device is configured to generate a superheated steam condition under the given conditions. The drying device can be a droplet separation column.

The steam generator comprises in particular a lower and an upper switching point for level control. The water level can be controlled, particularly by means of the level control, so that the steam generator does not run dry or overflow and thus steam of the desired quality can be provided.

It can be provided that when the filling level falls below a predetermined filling level, the steam generator or in particular the individually switched cartridges, each 5 KW, are automatically switched off to prevent dry running and glow through.

According to a further embodiment, the apparatus comprises multiple desorption vessels, wherein the steam generator is connected to respective steam inlets of the multiple desorption vessels. In an embodiment, the steam generator is connected to four desorption vessels. The maximum production rate of pure steam is 60 kg/h, 0.2 MPa (1 atmosphere gauge pressure). This is fully utilized in particular in parallel start-up operation of four desorption vessels. In subsequent operation, this is in particular then approximately one-third to one-half thereof. According to a further embodiment, the apparatus is configured to run the desorption vessels in parallel in varying numbers with a time delay of 1 to 2 min.

According to a further embodiment, the steam generator is configured to produce pure steam from demineralized water.

The fully demineralized water is, according to an embodiment, provided by a water treatment device upstream of the steam generator. This comprises in particular a city water infeed, in particular a softening installation and in particular downstream a reverse osmosis module. The treated water is, according to an embodiment, stored in a water storage tank connected to the steam generator. In particular, a pre-filter is installed between the city water infeed and the softening installation.

The pre-filter comprises, according to an embodiment, pores with a size of 50 μm to a maximum of 100 μm.

According to a further embodiment, the pre-filter comprises pores of a pore size ranging from 10 nm to 100 μm, in particular 100 nm to 100 μm, further in particular 1 μm to 100 μm, wherein in particular the pores can be of different sizes.

In particular a fine filter is arranged between the softening installation and the reverse osmosis module.

The pores of the fine filter are, according to an embodiment, 2 μm to 8 μm in size, wherein the pores may vary in size. In certain embodiments, the average size is 5 μm.

According to a further embodiment, the fine filter comprises pores of a pore size ranging from 10 nm to 8 μm, in particular 100 nm to 8 μm, further in particular 1 μm to 8 μm, wherein in particular the pores can be of different sizes.

According to a further embodiment, the apparatus comprises a condensate section, wherein the desorption vessel is connected to the condensate section, and wherein the condensate section is arranged to cool the secondary volume flow and to produce a condensate therefrom. A filter is arranged between the desorption vessel and the condensate section in particular.

This filter is configured in particular to filter out all particles entrained in the secondary volume flow and detached therefrom as they flow through the adsorbent. This filter can be flushed in particular. It is possible to arrange several of these filters in series.

In an embodiment, a pre-filter, in particular a rinsable pre-filter, and a post-filter, in particular a rinsable post-filter, are arranged between the desorption vessel and the condensate section, wherein the pre-filter is arranged upstream of the post-filter.

According to one embodiment, the pre-filter comprises a pore size of 15 μm to 30 μm, in particular of approx. 25 μm.

According to a further embodiment, the pre-filter comprises pores of a pore size ranging from 10 nm to 30 μm, in particular 100 nm to 30 μm, further in particular 1 μm to 30 μm, wherein in particular the pores can be of different sizes.

According to one embodiment, the post-filter comprises a pore size of 1 μm to 5 μm, in particular of about 5 μm.

According to a further embodiment, the post-filter comprises pores of a pore size in the region of 10 nm to 5 μm, in particular 100 nm to 5 μm, further in particular 1 μm to 5 μm, wherein in particular the pores can be of different sizes.

According to a further embodiment, the condensate section comprises a pre-cooler, an inter-cooler as well as an after-cooler, which are arranged in sequence. According to an embodiment, the pre-cooler and the inter-cooler are operated with (particularly uncooled) city water or are operable with (particularly uncooled) city water. The after-cooler is operated in particular with cooled city water or can be operated with cooled city water. A fine filter is particularly arranged between the inter-cooler and the after-cooler.

Alternatively, all coolers, i.e. the pre-cooler, the inter-cooler and the after-cooler, can also be operated with cooled city water, which can differ in temperature respective to the process control.

According to an embodiment, the fine filter comprises a pore size of 1 μm to 5 μm, in particular of about 5 μm.

According to a further embodiment, the fine filter comprises pores of a pore size ranging from 10 nm to 5 μm, in particular 100 nm to 5 μm, further in particular 1 μm to 5 μm, wherein in particular the pores can be of different sizes.

According to a further embodiment, the apparatus comprises a filter rinsing system, wherein the filter rinsing system is configured to rinse the pre-filter, the intermediate filter, the post-filter and/or the fine filter, in particular automatically. According to a further embodiment, the filter rinsing system is configured to rinse the pre-filter, the intermediate filter, the after-filter and/or the fine filter with different volumes of a rinsing liquid, in particular water (e.g. demineralized water, deionized water). According to a further embodiment, the filter rinsing system is designed to rinse the pre-filter, the intermediate filter, the post-filter and/or the fine filter with a time delay. The filter rinsing system is in particular connected to a storage tank for storing the rinsing liquid or comprises a storage tank for storing the rinsing liquid. In particular, the filter flushing system comprises a pump for pumping the flushing liquid from the storage tank through the pre-filter, the intermediate filter, the post-filter and/or the fine filter. The upper limit for the total volume for flushing the filters is calculated in particular from the volume of the storage tank minus a residual filling quantity which is dimensioned so that the pump does not run dry.

According to a further embodiment, the condensate section is followed by a collection section. This comprises in particular a condensate collection container, a compressed air generator as well as a buffer container.

The condensate collection container is connected in particular downstream of the after-cooler. This condensate collection container is configured in particular to collect the cooled condensate and separate it into its phases.

According to a further embodiment, the apparatus comprises a buffer container, wherein the apparatus is configured to transfer the halogenated hydrocarbons, which are separable from the water due to their density, into the buffer container by means of an outlet when a respective filling level is reached.

According to a further embodiment, the apparatus comprises a seal, in particular a circumferential seal, arranged or disposable in the space between the adsorbent container (or each adsorbent container) and the desorption vessel, which is formed to close the space, in particular in a gas-tight manner, when the adsorbent container is inserted into the desorption vessel and thus, in particular, to prevent a vapor flow in the space between the adsorbent container and the desorption vessel.

According to a further embodiment, the apparatus is configured to deform the seal by means of an overpressure (e.g., an inert gas, e.g., of up to 0.12 MPa above the process pressure prevailing in the desorbent vessel) such that the seal closes the space, in particular in a gas-tight manner (in particular wherein the seal is pressable against an outer wall of the adsorbent container or against an inner wall of the desorbent vessel by means of the overpressure).

According to an embodiment, the apparatus is configured to deform the seal only during the desorption step by means of the overpressure.

According to a further embodiment, a lid of the adsorbent container comprises the seal.

According to a further embodiment, the seal is designed as an inflatable profile seal.

According to a further embodiment, the desorption vessel comprises a bottom, wherein the bottom comprises a first shell and a second shell, wherein a space is designed between the first shell and the second shell, and wherein in particular the device is designed to introduce steam into the space during the sterilization step so that the bottom is heatable.

DESCRIPTION OF FIGURES

FIG. 1 shows a desorption vessel 100 comprising a circumferential wall 170 and a bottom 130 terminating with the circumferential wall 170, comprising two steam inlets 110a, 110b and a steam outlet 120 arranged at the bottom of the desorption vessel 130. A valve 140 is arranged at the steam outlet. This valve 140 is configured to open or close the outlet 190 downstream of the steam outlet 120. Two removable adsorbent containers 200a, 200b are arranged one above the other in the desorption vessel 100. The steam inlets 110a, 100b are arranged above the removable adsorbent containers 200a, 200b. A temperature sensor 150 is arranged between the steam outlet 120 and the lower adsorbent vessel 200b immediately below the lower adsorbent vessel 200b. This is connected to a control device 160.

FIG. 2 shows an adsorbent container 200. It comprises a circumferential wall 220, terminating with a bottom 230 and a lid 240. The bottom 230 and the lid 240 of the adsorbent container are provided with a filter fabric 250. A seal 210 is arranged on the lid 240 of the adsorbent container 200, which is adapted to close the space between the wall of the desorption vessel 170 and the adsorbent container 220 in a gas-tight manner when the adsorbent container is inserted into the desorption vessel.

FIG. 3 shows a schematic diagram of the recovery installation. The sterilization and desorption process takes place in the desorption vessels 100. Dry pure steam required for this purpose is provided in the steam generator 300 with downstream drying device 310. The drying device 310 can be a droplet separation column. The clean steam is produced from demineralized water. The demineralized water is provided in a purification device upstream of the steam generator 300, which is arranged to purify water from a city water infeed 410 in a first step by means of a softening installation 420 and in a second step by means of a reverse osmosis module 430. A pre-filter 450 is arranged between the city water infeed 410 and the softening installation 420. A fine filter 460 is arranged between the softener 420 and the reverse osmosis module 430. Subsequent to the reverse osmosis module 430, a water storage tank 440 is arranged to store the purified city water for use in the steam generator 300. The desorption vessels 100 are arranged between the steam generator 300 and a condensate section. The condensate section is configured to cool the gas mixture leaving the desorption vessel 100 in the desorption step to form a condensate. The condensate section comprises a pre-cooler 520, an inter-cooler 530 as well as an after-cooler 540. Upstream of the pre-cooler 520 are a pre-filter 510a and a post-filter 510b. A fine filter 550 is arranged between the inter-cooler 530 and the after-cooler 540.

Figure 1:
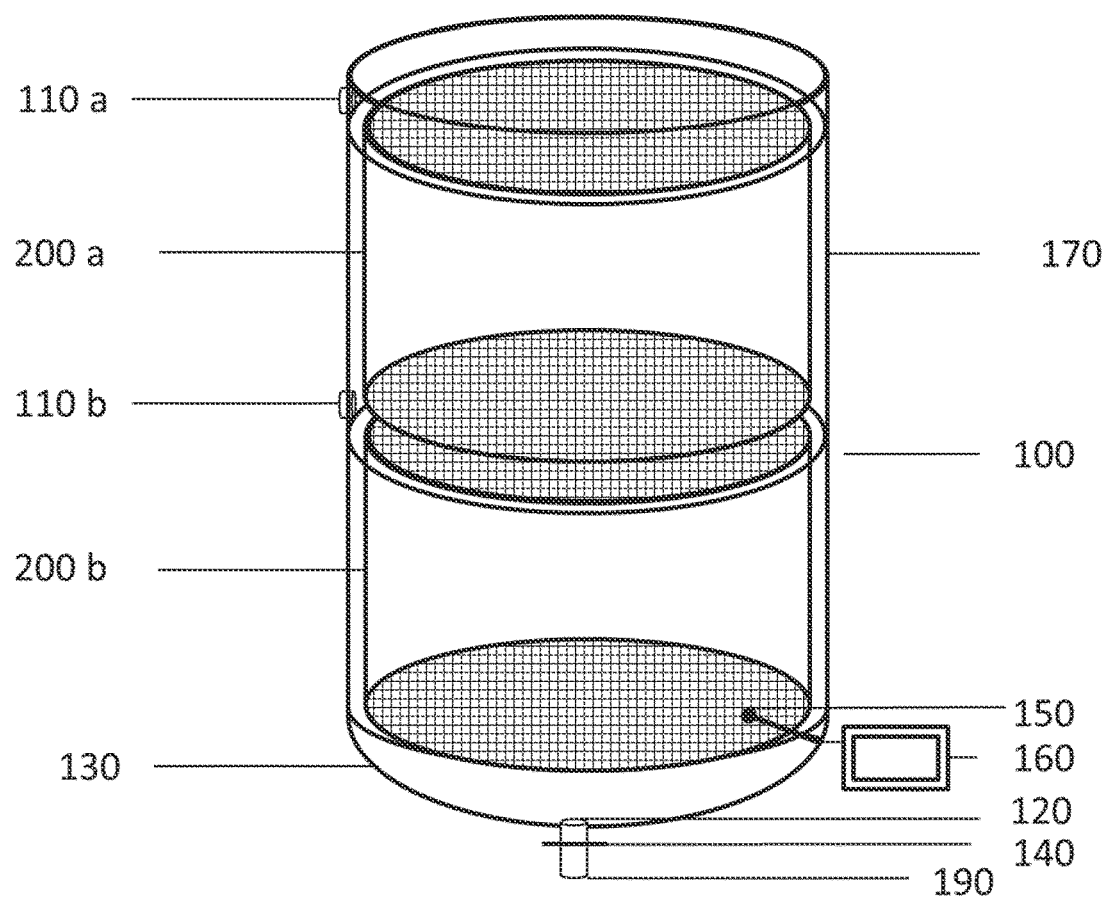
FIG. 1 shows a desorption vessel with two removable adsorbent containers.
Figure 2:
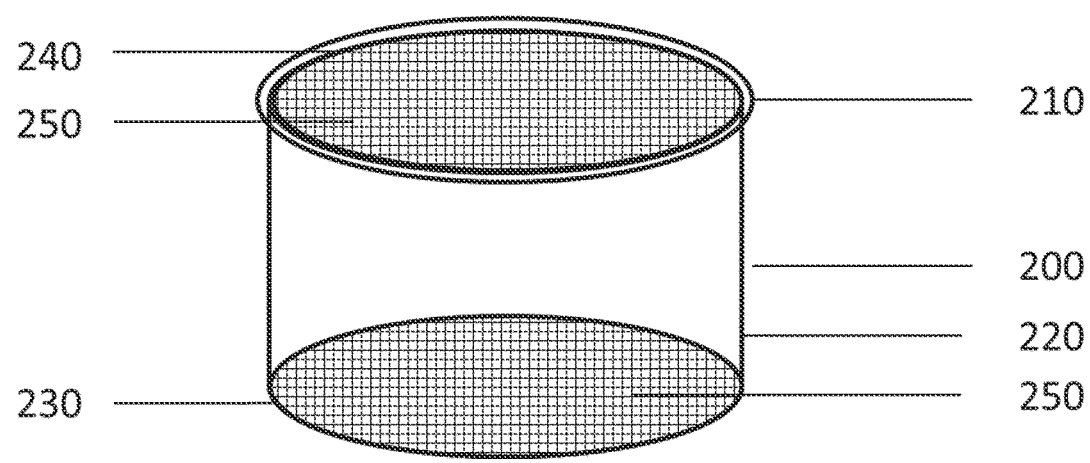
FIG. 2 shows an adsorbent container.
Figure 3:
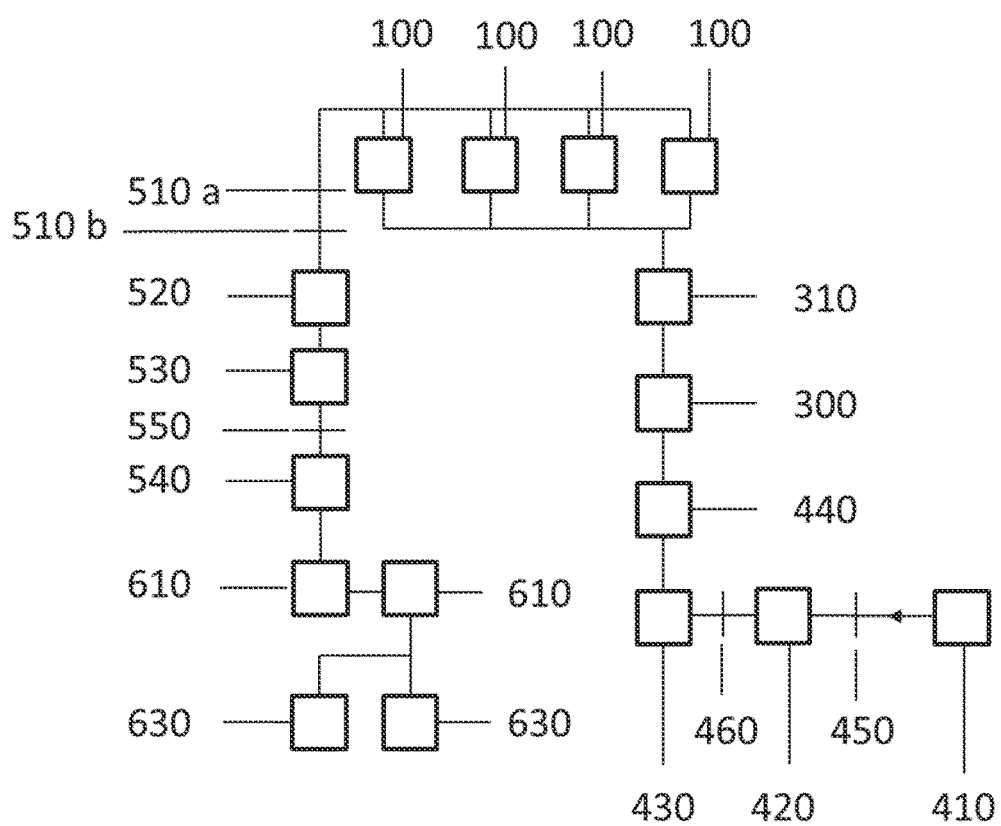
FIG. 3 shows a schematic diagram of the recovery installation.

A collection section adjoins the condensate section. One or more interconnected condensate collecting containers 610 are arranged downstream of the after-cooler 540 and are configured to collect the condensate passing through the after-cooler 540 and to separate it into its phases.

One or more buffer containers 630 can be connected to the condensate collection container 610, which are configured to receive the condensate separated into its phases. Alternatively, only a single condensate collecting container 610 (without additional buffer containers 630) can be provided, which can receive the entire condensate of a desorption step (in particular plus a certain amount of water required for separating the desorbate).

The removal of the desorbate from the desorption vessel 100 can take place in particular by means of utilizing the potential energy of the desorbate or, for example, by an impingement with an inert gas (e.g. nitrogen).

DESCRIPTION OF EXEMPLARY EMBODIMENTS

Example 1

The introduction of the superheated steam is divided into two phases. In the first phase, the superheated steam flows from the steam generator into the desorption vessel with the outlet valve closed until a pressure of 0.2 MPa or greater is reached. This pressure and the corresponding temperature are maintained for a period of 30 min. During this time, autoclave-like conditions prevail in the desorption vessel, ensuring complete inactivation of all pathogens present in the sorbate (bacteria, microplasmas, fungi, viruses, viroids, prions and/or parasites). This inactivation phase is followed by the desorption phase over a period of 120 min, during which, with the outlet valve open, a steady flow of superheated steam through the desorption vessel allows the halogenated hydrocarbons expelled from the sorbate to be absorbed and removed. This condensate-steam mixture is cleaned of the entrained impurities via a collector line by means of a rinsable pre-filter (stainless steel filter, 25 microns) and a rinsable post-filter (stainless steel, 5 microns) and brought to a temperature below 30 degrees by three successively connected coolers. Depending on the halogenated hydrocarbon to be desorbed, particularly inhalation anesthetic, this temperature difference can be adjusted as described above. After the last cooler, the condensate-water mixture is transferred to a condensate collection container.

Example 2

TABLE 1

Overview of the process data of various sterilization cycles.

| Experiment | Input T/° C. (+15 K) | $T_{min}$/° C. | $T_{max}$/° C. | Pressure/bar | Time / min | Germs |
|---|---|---|---|---|---|---|
| 1.1 | 121.11 (+15 K) | 80.6 | 127.56 | 2.4 | 28:46 min | Germs at all positions |
| 1.2 | 121.11 (+15 K) | 116.62 | 130.93 | 2.5 | 28:50 min | Germs at one position |
| 1.3 | 121.11 (+15 K) | 124.59 | 141.44 | 2.4 | 28:10 min | Germ-free at all position |
| 1.4 | 121.11 (+15 K) | 125.01 | 136.55 | 2.35 | 28:27 min | Germs at two position |
| 2.1 | 121.11 (+15 K) | 126.30 | 134.57 | 2.44 | 32:53 min | Germ-free at all position |
| 2.2 | 121.11 (+15 K) | 100.40 | 130.07 | N/A | 34:49 min | Germs at two position |
| 2.3 | 121.11 (+15 K) | 64.03 | 128.16 | 2.48 | 30:15 min | Germs at six position |
| 2.4 | 121.11 (+15 K) | 121.68 | 129.29 | 2.5 | 28:27 | Germ-free at all position |
| 2.5 | 121.11 (+15 K) | 127.25 | 131.34 | 2.5 | 30:22 | Germ-free at all position |

REFERENCE LIST 100 desorption vessel
110 steam inlet
110a first steam inlet
110b second steam inlet
120 steam outlet
130 bottom of the desorption vessel
140 valve
150 temperature sensor
160 control device
170 wall of the desorption vessel
190 outlet
200 adsorbent container
210 seal
220 wall of the adsorbent container
230 bottom of the adsorbent container
240 lid of the adsorbent container
250 filter fabric
300 steam generator
310 drying device
410 city water infeed
420 softening installation
430 reverse osmosis module
440 water storage tank
450 pre-filter
460 fine filter
510 filter
510a pre-filter
510b post-filter
520 pre-cooler
530 inter-cooler
540 after-cooler
550 fine filter
610 condensate collection container
620 compressed air generator
630 buffer container Items 1. Process for recovering halogenated hydrocarbons, wherein in a desorption step an adsorbent comprising adsorbed halogenated hydrocarbons is streamed through by water vapor, resulting in a secondary volume flow comprising halogenated hydrocarbons, and wherein the secondary volume flow is converted by cooling into a condensate containing halogenated hydrocarbons and water, from which the halogenated hydrocarbons are separated,
characterized in that
in a sterilization step preceding the desorption step, the adsorbent comprising adsorbed halogenated hydrocarbons is
for at least 10 min, in particular for 10 to 60 min,
at a temperature of more than 120° C., in particular from 121 to 150° C., and
at a pressure of from 0.15 MPa to 0.4 MPa, in particular from 0.15 to 0.3 MPa brought into contact with water vapor.

2. The process according to item 1, wherein during the sterilization step the adsorbent is not streamed through.

3. The process according to item 1 or 2, wherein the sterilization step and the desorption step are carried out in direct sequence in the same installation.

4. The process according to any of the preceding items, wherein the adsorbent is activated carbon, particularly hydrophobic activated carbon, and/or zeolite, particularly hydrophobic zeolite.

5. The process according to any of the preceding items, wherein the water vapor used in the desorption step contains essentially no liquid water, in particular less than 0.1 weight percent liquid water, further in particular no liquid water.

6. The process according to any of the preceding items, wherein the halogenated hydrocarbons comprise fluorine-containing inhalation anesthetics, particularly sevoflurane, isoflurane, enflurane, halothane, desflurane, or mixtures thereof.

7. The process according to any of the preceding items, wherein the adsorbent comprising the adsorbed halogenated hydrocarbons has been obtained by filtering respiratory air from the treatment of patients.

8. The process according to any of the preceding items, wherein the sterilization step is carried out for 20 to 40 min, in particular for about 30 min at a temperature of 135 to 145° C., and at a pressure of 0.24 to 0.26 MPa.

9. The process according to any of the preceding items, wherein the sterilization step and the desorption step are performed in a desorption vessel (100), and wherein the desorption vessel (100)
comprises a steam inlet (110) and a steam outlet (120), and
the adsorbent is arranged in the desorption vessel (100) between the steam inlet (110) and the steam outlet (120) such that steam entering the desorption vessel (100) through the steam inlet (110) must flow through the adsorbent before it leaves the desorption vessel (100) through the steam outlet (120).

10. The process according to item 9, wherein the desorption vessel (100) comprises a valve (140) subsequent to the steam outlet (120), wherein the valve (140) is closed during the sterilization step and is open during the desorption step.

11. The process according to any of items 9 or 10, wherein the adsorbent in the desorption vessel (100) is contained in an adsorbent container (200) removable from the desorption vessel.

12. The process according to one of items 9 to 11, wherein the desorption vessel (100) comprises a circumferential wall (170) and a bottom (130) terminating with the circumferential wall (170), wherein the bottom (130) is a curved bottom, in particular a dished bottom according to DIN 28011,
wherein the curvature of the bottom (130) forms a cavity below the adsorbent container (200), which is configured to receive the desorbate.

13. The process according to any of items 9 to 12, wherein the temperature prevailing in the desorption vessel (100) is measured by a temperature sensor (150), and wherein the temperature sensor (150) is located below the adsorbent container (200) introduced into the desorption vessel (100), in particular between the steam outlet (120) and the adsorbent container (200) introduced into the desorption vessel (100), in particular immediately below the adsorbent container (200) introduced into the desorption vessel (100).

14. The process according to any of items 9 to 13, wherein the desorption vessel (100) comprises two adsorbent containers (200a, 200b) arranged one above the other, and the adsorbent containers (200a, 200b) can be supplied with steam through two steam inlets (110a, 110b) arranged respectively above the adsorbent containers (200a, 200b).

15. The process according to any of items 9 to 14, wherein the adsorbent container (200) comprises a bottom (230) and/or a lid (240), wherein the bottom (230) and/or the lid (240) comprise or consist of a gas-permeable filter fabric (250).

16. An apparatus for carrying out a process according to any of the preceding items, comprising
a pressure-stable desorption vessel (100),
a steam inlet (110) arranged to admit water vapor into the desorption vessel (100)
a steam outlet (120) arranged to discharge water vapor from the desorption vessel (100), with an outlet pipe (190) arranged downstream of the steam outlet (120) in the direction of the steam outlet
a valve (140) by which the outlet (190) is closable,
a space designed to receive a bulk material.

17. The apparatus according to item 16, wherein the desorption vessel (100) comprises
an adsorbent container (200) for receiving the bulk material, and
a temperature sensor (150) arranged on the side of the adsorbent container (200) facing the steam outlet (120).

18. The apparatus according to item 17, wherein the temperature sensor (150) is connected to a control device (160) which is configured to open the valve (140) after a target temperature has been reached and/or after a preselected time period of 10 to 60 min has elapsed during which the target temperature is maintained.

19. The device according to any of items 17 or 18, wherein the desorption vessel (100) comprises a dished bottom (130), in particular a dished bottom according to DIN 28011.

20. The apparatus according to any of items 16 to 19, wherein the desorption vessel (100) is pressure stable to 0.4 MPa.

21. The apparatus according to any of items 16 to 20, wherein the desorption vessel is arranged to receive two adsorbent containers (200a, 200b) arranged one above the other, and is configured with two steam inlets (110a, 110b) arranged respectively above the adsorbent containers (200a, 200b).

22. The apparatus according to any of the items 16 to 21, comprising a steam generator (300) adapted to generate water vapor, wherein the steam generator (300) is in fluid communication with a steam inlet (110).

The invention claimed is:

1. Process for recovering fluorinated inhalation anesthetics,
wherein in a desorption step an adsorbent comprising adsorbed fluorinated inhalation anesthetics is streamed through by water vapor, resulting in a secondary volume flow comprising fluorinated inhalation anesthetics,
and wherein the secondary volume flow is converted by cooling into a condensate containing fluorinated inhalation anesthetics and water, from which the fluorinated inhalation anesthetics are separated,
characterized in that
in a sterilization step preceding the desorption step, the adsorbent comprising adsorbed fluorinated inhalation anesthetics is
for at least 10 min,
at a temperature of more than 120° C., and
at a pressure of from 0.15 MPa to 0.4 MPa, brought into contact with water vapor,
wherein the sterilization step and the desorption step are performed in direct sequence in the same installation,
wherein the sterilization step and the desorption step are performed in a desorption vessel (100), and wherein the desorption vessel (100) comprises a steam inlet (110) and a steam outlet (120), and the adsorbent is arranged in the desorption vessel (100) between the steam inlet (110) and the steam outlet (120) such that steam entering the desorption vessel (100) through the steam inlet (110) must flow through the adsorbent before it leaves the desorption vessel (100) through the steam outlet (120), and
wherein the desorption vessel (100) comprises a valve (140) subsequent to the steam outlet (120), wherein the valve (140) is closed during the sterilization step and is open during the desorption step.

2. The process according to claim 1, wherein in the sterilization step preceding the desorption step, the adsorbent comprising adsorbed fluorinated inhalation anesthetics is for 10 to 60 min.

3. The process according to claim 1, wherein the adsorbent comprising the adsorbed fluorinated inhalation anesthetics was obtained by filtering respiratory air from the treatment of patients.

4. The process according to claim 1, wherein the sterilization step is carried out
for 20 to 40 min,
at a temperature of 135 to 145° C., and
at a pressure of 0.24 to 0.26 MPa.

5. The process according to claim 4, wherein the sterilization step is carried out for about 30 min.

6. The process according to claim 1, wherein the desorption vessel (100) has a prevailing temperature measured by a temperature sensor (150), and wherein the temperature sensor (150) is located below the adsorbent container (200) introduced into the desorption vessel (100).

7. The process according to claim 6, wherein the temperature sensor (150) is located between the steam outlet (120) and the adsorbent container (200) introduced into the desorption vessel (100).

8. The process according to claim 6, wherein the temperature sensor (150) is located immediately below the adsorbent container (200) introduced into the desorption vessel (100).

9. The process according to claim 1, wherein the desorption vessel (100) comprises two adsorbent containers (200a, 200b) arranged one above the other, and the adsorbent containers (200a, 200b) can be supplied with steam through two steam inlets (110a, 110b) arranged respectively above the adsorbent containers (200a, 200b).

10. The process according to claim 1, wherein the adsorbent container (200) comprises a bottom (230) and/or a lid (240), wherein the bottom (230) and/or the lid (240) comprise or consist of a gas-permeable filter fabric (250).

11. The process according to claim 1, wherein the sterilization step is conducted at a temperature of 121 to 150° C.

12. The process according to claim 1, wherein the sterilization step is conducted at a pressure of from 0.15 MPa to 0.3 MPa.

* * * * *